US00PP25749P3

(12) United States Plant Patent
Desmond

(10) Patent No.: US PP25,749 P3
(45) Date of Patent: Jul. 28, 2015

(54) ***ERYSIMUM* PLANT NAMED 'HONEYBERRY'**

(50) Latin Name: *Erysimum×hybrida*
Varietal Denomination: HONEYBERRY

(71) Applicant: Andrew Desmond, Bognor Regis (GB)

(72) Inventor: Andrew Desmond, Bognor Regis (GB)

( * ) Notice: Subject to any disclaimer, the term of this patent is extended or adjusted under 35 U.S.C. 154(b) by 115 days.

(21) Appl. No.: 13/998,344

(22) Filed: Oct. 23, 2013

(65) Prior Publication Data

US 2015/0113690 P1 Apr. 23, 2015

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Barbara Campbell; Cochran Freund & Young LLC

(57) ABSTRACT

A new and distinct variety of *ERYSIMUM* plant named 'HONEYBERRY' which is characterized by compact freely-branching habit, variegated foliage, crimson and mauve sweetly scented flowers which are produced from spring until early summer. In combination these traits set 'HONEYBERRY' apart from all other existing varieties of *ERYSIMUM* known to the inventor.

2 Drawing Sheets

Genus and species: Genus: *ERYSIMUM*. Species: ×*hybrida*.

Denomination: Denomination: 'HONEYBERRY'.

BACKGROUND OF THE INVENTION

The present invention relates to a new and distinct cultivar of *Erysimum*, also commonly known as perennial wallflower, which is grown as an ornamental for use in planted containers and in the garden and landscape. The new cultivar is known botanically as *Erysimum×hybrida*, and will be referred to hereinafter by the cultivar name 'HONEYBERRY'.

'HONEYBERRY' arose and was discovered by the inventor in 2009 as a naturally occurring variegated branch sport on a single plant in a crop of *Erysimum* plants which had been raised from seed at the inventor's nursery in Walberton, West Sussex, United Kingdom. The seeds were unnamed and all plants raised from the seed were non-variegated, except for the single plant with the observed variegated branch sport.

'HONEYBERRY' was first asexually propagated by the inventor in 2010 in Walberton, West Sussex, England. Asexual propagation was accomplished using softwood cuttings. Since that time, under careful observation, the distinguishing characteristics of 'HONEYBERRY' have been determined stable and uniform, and to reproduce true to type in successive generations of asexual propagation.

SUMMARY OF THE INVENTION

The distinguishing characteristics of 'HONEYBERRY' are as follows: In combination these traits set 'HONEYBERRY' apart from all other existing varieties of *Erysimum* known to the inventor. 'HONEYBERRY' has not been tested under all possible conditions and phenotypic differences may be observed with variations in environmental, climatic, and cultural conditions.

1. 'HONEYBERRY' is hardy and perennial in USDA Zone 7 and warmer.

2. The growth habit of 'HONEYBERRY' is compact and freely-branching.
3. The foliage of 'HONEYBERRY' is variegated, consisting of bright yellow colored margins on gray-green leaves.
4. The buds and opening flowers of 'HONEYBERRY' are crimson in color.
5. The fully open flowers of 'HONEYBERRY' are light mauve in color.
6. 'HONEYBERRY' blooms from spring until early summer.
7. 'HONEYBERRY' achieves a height of 30 cm and a spread of 20 cm in the first year of growth.
8. 'HONEYBERRY' achieves a height of 30 cm-40 cm and a spread of 30 cm-40 cm when mature and established as a perennial.
9. 'HONEYBERRY' grows well in full sun to part shade, in fertile well-drained soil.

COMPARISON WITH KNOWN VARIETY

The only other cultivar of variegated *Erysimum* known to the inventor is the variety 'WALFRASTAR' (U.S. Plant Pat. No. 23,101). 'HONEYBERRY' and 'WALFRASTAR' may be distinguished by flower color. Whereas the flowers of 'WALFRASTAR' are yellow in color, the flowers of 'HONEYBERRY' are crimson in color when opening, becoming light mauve when fully expanded.

BRIEF DESCRIPTION OF THE DRAWINGS

The accompanying color drawings illustrate the overall appearance of 'HONEYBERRY' showing the colors of its foliage and flowers as true as it is reasonably possible to obtain in colored reproductions of this type. Both drawings have been made from a one year old plant.

BOTANICAL DESCRIPTION OF THE PLANT

Figure 1:
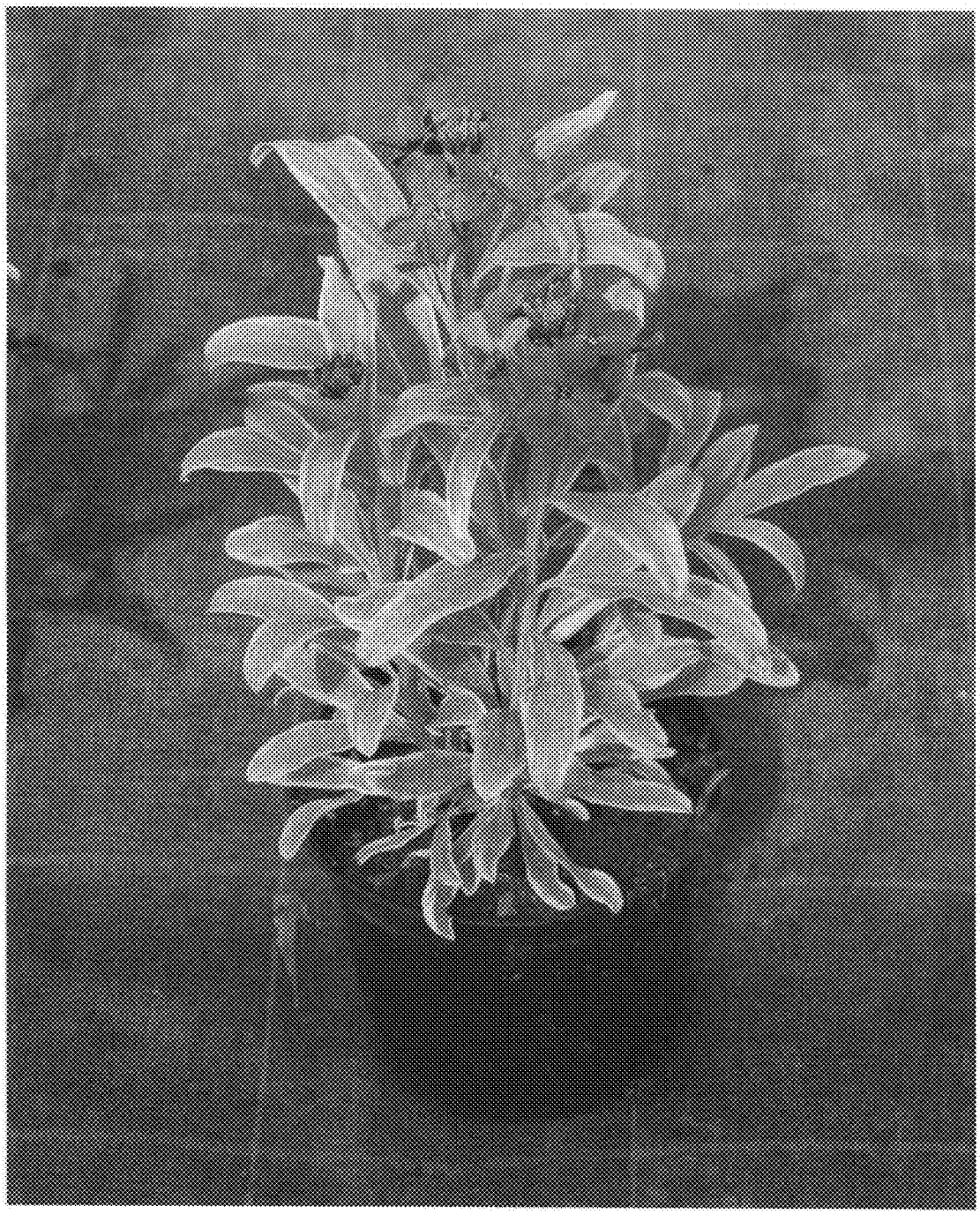
FIG. 1 depicts a whole plant of 'HONEYBERRY' at time of first flowering, in the spring. The illustrated plant has been grown in a 1 liter container in a frost-free greenhouse at the inventor's nursery in Walberton, West Sussex, England.
Figure 2:
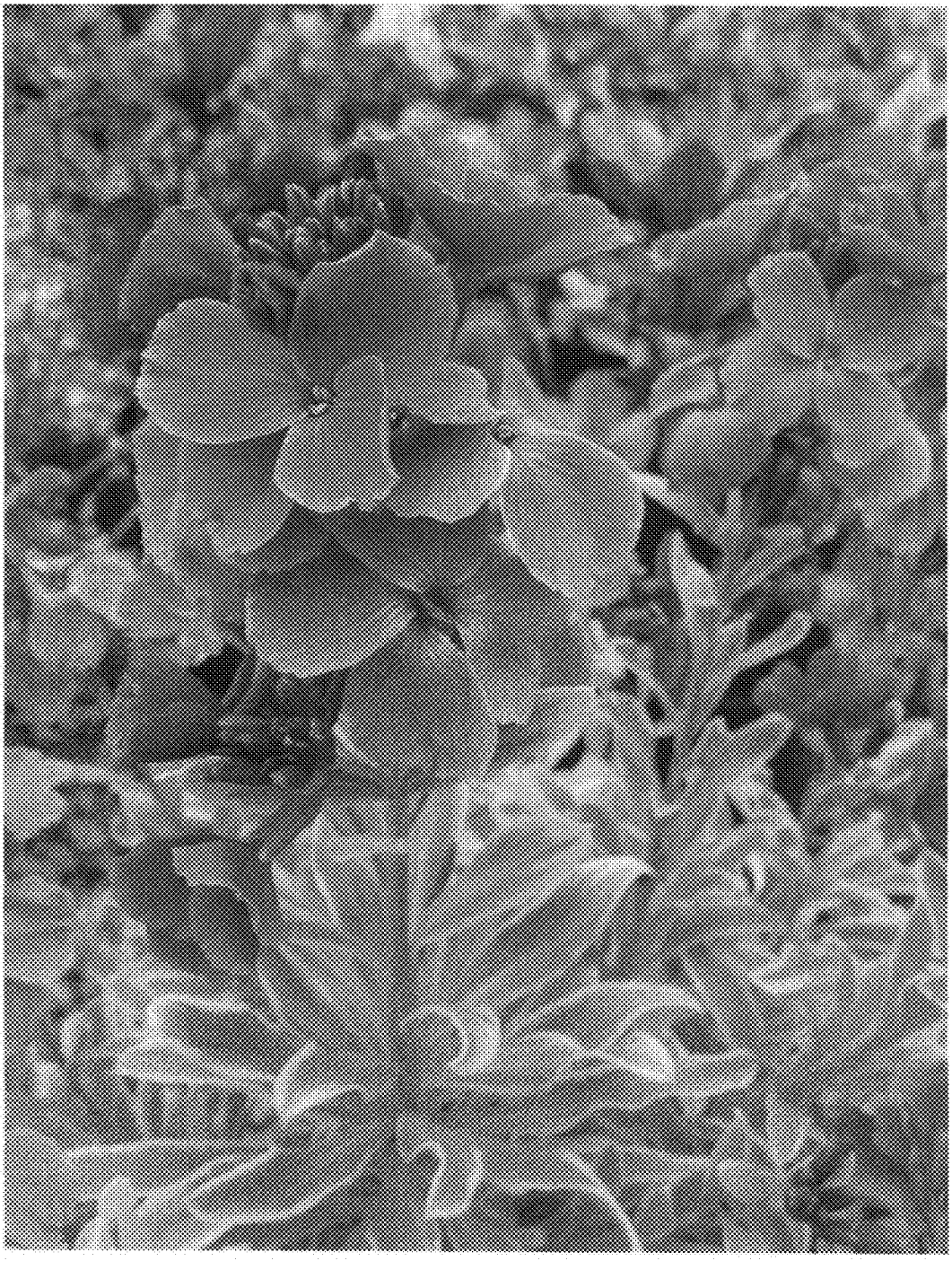
FIG. 2 depicts a close-up view of the inflorescence of 'HONEYBERRY' and depicts the crimson buds and the flowers which are crimson when opening, becoming light mauve when fully open.

The following is a detailed description of 'HONEYBERRY' as grown in a one liter container in a frost-free greenhouse in West Sussex, United Kingdom. The color determinations are in accordance with the 2007 edition of the Colour Chart of The Royal Horticultural Society, London, England, except where general color terms of ordinary dictionary significance are used. Growing conditions are similar to those of other *Erysimum.*

Botanical classification:

*Genus.*—*Erysimum.*

*Species.*—×*hybrida.*

Cultivar: 'HONEYBERRY'.

Commercial classification: Perennial.

Common name: Wallflower.

Use: Ornamental for container or landscape.

Cultural requirements: Plant in full sun or partial shade and any free-draining soil.

Particular pest resistance or susceptibility: None observed.

Particular disease resistance or susceptibility: In common with other varieties of *Erysimum*, 'HONEYBERRY' is susceptible to the plant bacterium *Xanthomonas.*

Parentage: 'HONEYBERRY' was discovered as a naturally occurring variegated branch sport on a single plant in a crop of *Erysimum* plants which had been raised from unnamed seed of *Erysimum.*

Plant description:

*Bloom period.*—Main period of bloom is from late March until June or July. Flowering may return in late summer and continue sporadically until October.

*Plant habit.*—Compact and freely branching.

*Vigor.*—Moderate.

*Height.*—30 cm.

*Width.*—20 cm.

*Hardiness.*—USDA Zones 7-10.

*Root system.*—Fine.

*Propagation.*—Propagation is accomplished using softwood cuttings at 20° Celsius base temperature.

*Time to develop roots.*—Roots are produced within 3 weeks.

*Crop time.*—Eight months are required to produce a finished one liter container from a rooted cutting.

Stem:

*Shape.*—Round.

*Stem color.*—143C.

*Average stem dimensions.*—25 cm. in length and 0.50 cm. in diameter.

*Stem surface.*—All stem surfaces finely and densely pubescent, color of pubescence 190D.

*Branching.*—Basal branching.

*Basal branch dimensions.*—2.50 cm. in diameter and 15 cm. in length.

*Basal branch color.*—143C.

*Internode distance.*—Ranges from 0.25 cm to 1.5 cm.

Foliage:

*Type.*—Evergreen.

*Shape.*—Lanceolate.

*Division.*—Simple.

*Apex.*—Acute.

*Base.*—Attenuate.

*Venation.*—Pinnate with central vein depressed on upper surface and protruding on lower surface.

*Vein color* (*upper and lower surfaces*).—138D.

*Margins.*—Entire, smooth.

*Arrangement.*—Alternate.

*Attachment.*—Sessile.

*Surfaces* (*adaxial and abaxial*).—Slightly pubescent.

*Leaf dimensions.*—5-10 cm. in length and 8-15 mm. in width.

*Leaf color* (*both surfaces*).—Ranges between and including 141D and 143C, except for margins and occasional streaking of margin into leaf blade.

*Leaf margins.*—Extend 1-3 mm inward from edge. Occasional streaking of margin color into leaf blade.

*Margin color.*—6C.

*Leaf fragrance.*—Absent.

Inflorescence and flowers:

*Inflorescence type.*—Cruciferous with bractless racemes.

*Inflorescence shape.*—Cruciform.

*Inflorescence dimensions* (*at maturity*).—15-25 cm. in length and 5-8 cm. in diameter.

*Flowers.*—Dimensions: 20 mm. in width and 8-10 mm. in height. Persistent or self-cleaning: Self-cleaning. Aspect: Erect and facing upward. Quantity: Numerous per inflorescence. 8-15 flowers are evident (in bud, opening and fully open) at any one time. A single inflorescence produces 40-50 flowers during the summer months. Throat depth: 6-9 mm. Lastingness: 7-10 days on the plant. Fragrance: Medium sweet fragrance as typical of wallflowers. Sexuality: Bisexual. Bud dimensions: 3-4 mm. in width and 6-9 mm. in length. Bud shape: Ovate. Bud color: Closest to N57A. Flower color: Opening N57A, becoming 67A when first fully open and N74C prior to senescence. Petals: Four in number. Fused or unfused: Unfused. Petal dimensions: 8 mm. in length and 8 mm. in width with further 8 mm.×1 mm. inside the calyx. Petal shape: Orbicular. Petal apex: Rounded. Petal base: Attenuate. Petal color (both surfaces): As flower opens, N57A; becoming 67A when first fully open and N74C prior to senescence. Petal margin: Entire. Petal surface: Glabrous. Petal veining: Pinnate, moderately prominent on both surfaces of open flowers, color 71A. Calyx dimensions: 3-4 mm. in diameter, 10 mm. in length. Calyx surface: Pubescent. Sepals: Four in number. Sepals fused or unfused: Unfused. Sepal margin: Entire. Sepal shape: Lanceolate. Sepal apex: Acute. Sepal color (both surfaces): Ranges between 58B and 58D. Sepal dimensions: 8 mm. in length and 2 mm. in width. Peduncle dimensions: 4-6 mm. in length and 1 mm. in diameter. Peduncle color: 145B. Peduncle surface: Pubescent. Pedicel dimensions: 6 mm. in length, 1 mm. in diameter. Pedicel color: 58B.

Reproductive organs:

*Stamens.*—Six in number: four stamens are longer, two are shorter.

*Stamen color.*—8C.

*Stamen dimensions.*—Four stamens are longer, 8 mm. in length and two stamens are shorter, 5 mm in length. Stamen diameter 0.5-1.0 mm.

*Anther color.*—11B.
*Anther shape.*—Rectangular.
*Anther dimensions.*—0.5 mm. in width and 2 mm. in length.
*Pollen color.*—11B.
*Amount of pollen.*—Small amount.
*Pistil.*—One.
*Pistil length.*—8 mm. in length.
*Pistil shape.*—Club-shaped.
*Pistil color.*—151C.
*Stigma shape.*—Reniform, spreading.
*Stigma color.*—151C.
*Stigma dimensions.*—length 1.5 mm, width 1 mm, height 1 mm.
*Style color.*—151B.
*Style length.*—2 mm. in length.
*Ovary position.*—Superior.
*Ovary color.*—191C.
*Ovary shape.*—Long, narrow and cylindrical.
*Ovary dimensions.*—5 mm. in height and 1.5 mm. in diameter.

Seed production: None observed.

I claim:

1. A new and distinct variety of *Erysimum* plant designated 'HONEYBERRY' as shown and described herein.

* * * * *